United States Patent [19]

Lorusso et al.

[11] Patent Number: 4,474,805

[45] Date of Patent: Oct. 2, 1984

[54] FUNGICIDAL COMPOSITIONS EMPLOYING SYNERGISTIC MIXTURES OF PHENYLACETAMIDE DERIVATIVES AND ZINEB OR MANCOZEB

[75] Inventors: Simone Lorusso; Luigi Mirenna, both of Milan; Anacleto Dal Moro, Treviso, all of Italy

[73] Assignee: Montedison S.p.A., Milan, Italy

[21] Appl. No.: 509,653

[22] Filed: Jun. 30, 1983

[30] Foreign Application Priority Data

Apr. 22, 1980 [IT] Italy ............................... 21537 A/80

[51] Int. Cl.³ .................... A01N 43/36; A01N 47/10; A01N 59/20
[52] U.S. Cl. ................................... 424/286; 424/141; 424/274
[58] Field of Search .......................................... 424/286

[56] References Cited

U.S. PATENT DOCUMENTS 4,060,625 11/1977 Klopping ............................. 424/286
4,291,049 9/1981 Bosone et al. ....................... 424/309

OTHER PUBLICATIONS

Colby, *Weeds* 15(1), pp. 20–22, (1967).

*Primary Examiner*—Allen J. Robinson

[57] ABSTRACT

Synergistic mixtures of fungicidal N-(2,6-dimethylphenyl)-N-(1-methoxycarbonyl-ethyl)-phenylacetamide with other selected fungicides which are ethylene-bis-dithiocarbamates, N-trichloromethylthio-imides or copper oxychloride are disclosed as are compositions comprising the synergistic mixtures.

Said mixtures and compositions are effective in controlling fungi infections of useful plants.

5 Claims, No Drawings

FUNGICIDAL COMPOSITIONS EMPLOYING SYNERGISTIC MIXTURES OF PHENYLACETAMIDE DERIVATIVES AND ZINEB OR MANCOZEB

This application is a continuation in part of application Ser. No. 256,234 filed Apr. 21, 1981, now abandoned.

BACKGROUND OF THE INVENTION

The fungicidal compound N-(2,6-dimethyl-phenyl)-N-(1-methoxy-carbonyl-ethyl)-phenylacetamide of formula:

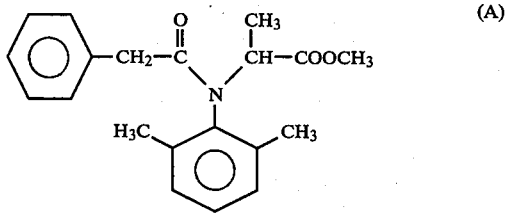

has been disclosed in Italian patent application No. 25295 A/78 assigned to Montedison, S.p.A., and which is a priority document in Bosone et al. U.S. Pat. No. 4,291,049, issued Sept. 22, 1981.

Compound A is a fungicide endowed with a remarkable anti-mildew activity, a low phytotoxicity and systemic action.

This last characteristic, which is useful in many respects in combatting fungi, presents however, a drawback common to all the systemic fungicides. In fact, when the plant's vegetative activity decreases, the systemic fungicide is less movable and consequently less effective.

Because of this drawback, it is desirable to coformulate the systemic product with other non-systemic fungicides.

THE PRESENT INVENTION

It is an object of this invention to provide formulations comprising fungicide (A) with selected non-systemic fungicides which formulations exhibit synergism.

In the course of our studies of co-formulations of fungicide (A) we have found, surprisingly, that the coformulation of (A) with fungicides belonging to, and selected from, dithiocarbamates, N-haloalkylthio-imides, or copper oxychloride results in a synergistic mixture thereof which is remarkably more effective than the individual compounds at the considered doses. Accordingly, the present invention provides synergistic mixtures of fungicide A (N-2,6-dimethylphenyl)-N-(1-methoxycarbonyl-ethyl)-phenyl-acetamide) and particular and selected non-systemic fungicides belonging to the following groups or classes:

B—dithiocarbamates;
C—N-haloalkylthio-imides; and
D—copper oxychloride.

Useful dithiocarbamates (group B) comprise, for example:

Zineb: zinc ethylene-bis-dithiocarbamate;
Maneb: manganese ethylene-bis-dithiocarbamate;
Nabam: sodium ethylene-bis-dithiocarbamate;
Mancozeb: a coordination compound of zinc ions with manganese ethylene-bis-dithiocarbamate, in which the ratio between zinc ions and manganese ions is 1:8;
Propineb: zinc 1,2-propylene-bis-dithiocarbamate.

N-haloalkylthio-imides (group C) comprise for example:

Folpet: compound N-trichloromethylthio-phthalimide;
Captan: compound N-trichloromethylthio-$\Delta^4$-tetrahydrophthalimide;
Captafol: compound N-(1,1,2,2-tetrachloroethylthio)-$\Delta^4$-tetrahydrophthalimide.

In the synergistic mixtures of the invention, components B, C or D are present in amounts of from 3 to 1,000 times the amount of component A.

In particular, component B is Zineb or Mancozeb and is present in amounts of from 3 to 200 times the amount of component A.

This invention also provides fungicidal compositions containing the synergistic mixtures as active principle and which compositions contain the mixture of the two active principles (compound A and compounds of groups B, C or D) in amounts of from 3 to 90% by weight.

Said compositions are effective in fighting fungi infections of useful plants such as, for example, vine, tobacco, tomato, potato and other horticultural cultivations.

The most important class of fungi, due to the damages caused, and which can be successfully fought by using the synergistic mixtures and compositions containing them, of this invention is that of Phycomycetes which comprises *Plasmopara spp., Phytophtora spp., Peronospora spp., Pseudoperonospora spp.* and *Phytium spp.*

The fungicidal compositions of the present invention contain, besides the active synergistic mixture, other inert carrier and, optionally, additives. The components are chosen mainly as a function of the composition to be prepared. For example, for preparing a dry powder it may be sufficient to add only an inert solid such as kieselguhr, kaolin, talc, colloidal silica, sodium or calcium carbonate.

To prepare a wettable powder, it it within the scope of this invention to add to the mixture of active substances:

inert carriers such as kieselguhr, (fossil-flour), kaolin, talc, colloidal silica;
wetting agents such as alkylaromatics, alkylphenols, polyoxyethylates or sorbitan oleates;
dispersants such as lignin-sulphonates or polymethacrylates.

The compositions so obtained are effective in doses comprised between 1 and 30 Kg/ha.

The choice of the most suitable compositions, and of the application doses, depends on various factors, such as the type of fungus to be fought and the culture to be treated, environment factors, availability of application means, etc.

The following examples are given to illustrate our invention in more detail but are not intended to be limiting.

EXAMPLE 1

Methodology for determining the preventive fungicidal activity against *Plasmopara viticola* (B et C) Berl et de Toni, on vine plants.

Vine plants c.v. Dolcetto, cultivated in pots in a conditioned environment at 25° C. and 60% of relative humidity, were sprayed, on both faces of the leaves, with a hydroacetonic suspension (20% by volume of acetone) of the products being tested.

One day after the treatment the lower faces of the leaves were sprayed with an aqueous suspension of conides of Plasmopara v. (200,000 conides per cc.) and were then kept for 24 hours in a humidity-saturated room at 21° C.

The plants were then transferred to a room conditioned at 21° C. and 70% of relative humidity for the fungus incubation period (7 days).

At the end of said period, the damages caused to the plants were determined on the basis of the leaf surface (lower faces) covered with conide formations of the fungus.

The fungicidal activity was expressed as reduction in percent of the fungine infection in comparison with infected, but not preventively treated plants, and it was expressed according to a scale of values ranging from 100 (sound plant) to 0 (fully infected plant).

EXAMPLE 2

Synergistic effect.

The synergistic effect of the fungicidal compounds in admixture with one another was established from the better activity of the mixture of the two components as compared with the theoretical activity of a non-synergistic mixture of the two components in the same ratios.

The theoretical fungicidal activity expressed as percentage of reduction of the infection [X(%)] of a non synergistic mixture was calculated by the following formula:

$$X(\%) = a(\%) + \frac{[100 - a(\%)] \cdot b(\%)}{100}$$

wherein:
- a (%) = fungicidal activity of a pure component at the considered dose, expressed as percentage of infection reduction;
- b (%) = fungicidal activity of the other pure component at the considered dose, expressed as percentage of infection reduction.

The data reported refer to the preventive activity against Plasmopara viticola on vine plants.

The values of a (%) and b (%) were obtained as described in Example 1.

Synergism of fungicide N-(2,6-dimethylphenyl)-N-(1-methoxy-carbonyl-ethyl)-phenylacetamide (A) and fungicide Zineb in admixture with each other.

| Fungicidal activity of A [a (%)] | |
|---|---|
| dose (°/oo) | activity |
| 0.001 | 58 |
| 0.0005 | 28 |

| Fungicidal activity of Zineb [b (%)] | |
|---|---|
| dose (°/oo) | activity |
| 0.1 | 30 |
| 0.05 | 24 |
| 0.01 | 15 |
| 0.003 | 10 |

The fungicidal activity of mixtures of A and Zineb is recorded in Table I.

TABLE I

| A:Zineb ratio | A (°/oo) | Zineb (°/oo) | Theoretical activity (X %) | Found activity (%) |
|---|---|---|---|---|
| 1:100 | 0.001 | 0.1 | 70.6 | 100 |
| 1:50 | 0.001 | 0.05 | 68.8 | 87 |
| 1:10 | 0.001 | 0.01 | 64.3 | 87 |
| 1:200 | 0.0005 | 0.1 | 49.6 | 100 |
| 1:100 | 0.0005 | 0.05 | 45.28 | 88 |
| 1:20 | 0.0005 | 0.01 | 38.8 | 61 |
| 1:3 | 0.001 | 0.003 | 62.2 | 75 |

Synergism of compound A and Mancozeb in admixture with each other.

| Fungicidal avitivity of Mancozeb (b %) | |
|---|---|
| dose (°/oo) | activity |
| 0.05 | 80 |
| 0.01 | 14 |
| 0.003 | 10 |

The fungicidal activity of mixtures of A and Mancozeb is recorded in Table II.

TABLE II

| A:Mancozeb ratio | A (°/oo) | Mancozeb (°/oo) | Theoretical activity [X (%)] | Found activity (%) |
|---|---|---|---|---|
| 1:50 | 0.001 | 0.05 | 91.6 | 100 |
| 1:10 | 0.001 | 0.01 | 63.88 | 88 |
| 1:100 | 0.0005 | 0.05 | 85.6 | 100 |
| 1:20 | 0.0005 | 0.01 | 38.08 | 58 |
| 1:3 | 0.001 | 0.003 | 62.2 | 72 |

Synergism of compound A and Captafol in admixture with each other.

| Fungicidal activity of Captafol (b %) | |
|---|---|
| dose (°/oo) | activity (%) |
| 0.05 | 90 |
| 0.01 | 65 |
| 0.001 | 50 |

The fungicidal activity of mixtures of A and Captafol is shown in Table III.

TABLE III

| A (°/oo) | Captafol (°/oo) | Theoretical activity [X (%)] | Found activity (%) |
|---|---|---|---|
| 0.001 | 0.05 | 95.8 | 100 |
| 0.001 | 0.01 | 85.3 | 100 |
| 0.001 | 0.001 | 79.0 | 90 |
| 0.0005 | 0.05 | 92.8 | 100 |
| 0.0005 | 0.01 | 74.8 | 90 |
| 0.0005 | 0.001 | 64.0 | 70 |

Synergism of compound A and copper oxychloride in admixture with each other.

| Fungicidal activity of copper oxychloride (b %) | |
|---|---|
| dose (°/oo) | activity (%) |
| 0.1 | 45 |
| 0.05 | 42 |
| 0.01 | 32 |

The fungicidal activity of mixtures of A and copper oxychloride is recorded in Table IV.

TABLE IV

| A (°/oo) | Copper oxychloride (°/oo) | Theoretical activity [X (%)] | Found activity (%) |
|---|---|---|---|
| 0.001 | 0.1 | 77.0 | 85 |
| 0.001 | 0.05 | 75.7 | 80 |
| 0.001 | 0.01 | 71.5 | 74 |
| 0.0005 | 0.1 | 60.0 | 75 |
| 0.0005 | 0.05 | 58.2 | 65 |
| 0.0005 | 0.01 | 51.1 | 60 |

EXAMPLE 3

Methodology for determining the preventive fungicidal activity on tobacco mildew. *Peronospora tabacina* Adam.

The leaves of tobacco plants cv. Burley, cultivated in mixture pot in a conditioned environment, were treated by spraying onto both leaf faces the mixture being tested in a hydroacetonic solution at 20% of acetone (vol./vol.).

2 days after said treatment the leaves were sprayed on their lower faces with an aqueous suspension of conids of *Peronospora tabacina* (200,000 conids/cc.).

After a 6-hour residence period in a humidity-saturated environment, the plants were transferred to a conditioned environment at 20° C., and 70% of relative humidity for the incubation of the fungus. At the conclusion of the incubation period (6 days), the seriousness of the infection was evaluated at sight according to indexes of an evaluation scale ranging from 100 (sound plant) to 0 (fully infected plant).

EXAMPLE 4

Synergistic effect.

The synergistic effect of the fungicidal compounds was calculated as described in example 2.

The data reported hereinbelow refer to the preventive activity against *Peronospora tabacina* on tobacco mildew. The values of a (%) and b (%) were obtained as described in example 3.

Synergism of fungicide N-(2,6-dimethylphenyl)-N-(1-methoxy-carbonyl-ethyl)-phenylacetamide (A) and fungicide Zineb in admixture with each other.

| Fungicidal activity of A [a (%)] | |
|---|---|
| dose (°/oo) | activity |
| 0.001 | 75 |
| 0.0005 | 50 |

| Fungicidal activity of Zineb [b (%)] | |
|---|---|
| dose (°/oo) | activity |
| 0.1 | 45 |
| 0.05 | 38 |
| 0.01 | 30 |
| 0.003 | 25 |

The fungicidal activity of mixtures of A and Zineb is recorded in Table V.

TABLE V

| A:Zineb ratio | A (°/oo) | Zineb (°/oo) | Theoretical activity (X %) | Found activity (%) |
|---|---|---|---|---|
| 1:100 | 0.001 | 0.1 | 86.25 | 100 |
| 1:50 | 0.001 | 0.05 | 84.5 | 100 |
| 1:10 | 0.001 | 0.01 | 82.5 | 100 |
| 1:200 | 0.0005 | 0.1 | 72.5 | 95 |
| 1:100 | 0.0005 | 0.05 | 69.0 | 90 |
| 1:20 | 0.0005 | 0.01 | 65.0 | 85 |
| 1:3 | 0.001 | 0.003 | 81.25 | 93 |

Synergism of compound A and Mancozeb in admixture with each other.

| Fungicidal activity of Mancozeb (b %) | |
|---|---|
| dose (°/oo) | activity (%) |
| 0.05 | 70 |
| 0.01 | 35 |
| 0.003 | 28 |

The fungicidal activity of mixtures of A and Mancozeb is recorded in Table VI.

TABLE VI

| A:Mancozeb ratio | A (°/oo) | Mancozeb (°/oo) | Theoretical activity [X (%)] | Found activity (%) |
|---|---|---|---|---|
| 1:50 | 0.001 | 0.05 | 92.5 | 100 |
| 1:10 | 0.001 | 0.01 | 83.75 | 100 |
| 1:100 | 0.0005 | 0.05 | 85.0 | 100 |
| 1:20 | 0.0005 | 0.01 | 67.5 | 90 |
| 1:3 | 0.001 | 0.003 | 82.0 | 100 |

EXAMPLE 5

Preparation of compositions in wettable powder.

General method: the various components of the composition were mixed with other another and homogenized by grinding in an air jet mill till obtaining particles having average sizes of 5-6 micron.

Following the abovesaid operative modalities the compositions recorded on following Tables VII and VIII were prepared.

TABLE VII

Fungicidal composition in wettable powder (the amounts of the components are expressed in percent by weight)

| Components | 1 | 2 | 3 | 4 | 5 | 6 | 7 | 8 | 9 | 10 |
|---|---|---|---|---|---|---|---|---|---|---|
| Active ingredient | | | | | | | | | | |
| Compound A | 25 | 5 | 5 | 4 | 5 | 1 | 8 | 17 | 17 | 11 |
| Zineb | | 50 | | | | 10 | 80 | 54 | | |
| Mancozeb | | | 50 | | | | | | 54 | 70 |
| Copper oxychloride | | | | 80 | | | | | | |
| Folpet | | | | | 50 | | | | | |
| Inert carriers | | | | | | | | | | |
| kaolin | 70 | 39 | 40 | 4 | | 83 | 4 | 23 | 23 | 9 |
| synthetic silica | | | | 6 | | | | | | 4 |
| kieselguhr | | | | | 40 | | | | | |
| Additives (surfactants) | | | | | | | | | | |
| sodium alkylnaphthalene sulphonate | 1 | | 1 | | 1 | 2 | | | 1 | |
| sodium alkyl-sulphosuccinate | | 2 | | 2 | | | 2 | 2 | | 2 |
| sodium lignin-sulphonate | | 2 | | 4 | | 4 | | 3 | 3 | |
| sodium polymethacrylate | 4 | 2 | 4 | | 4 | | 3 | 4 | 2 | 4 |

TABLE VIII

Fungicidal compositions in wettable powder (the amounts of components are expressed in percent by weight).

| Components | Composition No. | | | |
| --- | --- | --- | --- | --- |
|  | 11 | 12 | 13 | 14 |
| *Active ingredients* | | | | |
| Compound A | 8 | 17 | 8 | 17 |
| Zineb | 65 | 54 | | |
| Mancozeb | | | 65 | 54 |
| *Inert carriers* | | | | |
| Kaolin | 20.5 | 22.5 | 19.5 | 21.5 |
| Synthetic silica | 1.5 | 1.5 | | |
| Kieselguhr | | | | |
| *Additives (surfactants)* | | | | |
| Sodium alkylnaphthalene sulphonate | | | | |
| Sodium alkylsulphosuccinate | 1 | 1 | 1 | 1 |
| Sodium lignin-sulphonate | 4 | 4 | 4.5 | 4.5 |
| Sodium polymethacrylate | | | 2 | 2 |

EXAMPLE 6

Preparation of compositions in dry powder.

General method: The composition components were mixed with one another and homogenized by grinding in a mechanical impact stud mill.

Operating according to the abovecited operative modalities, the compositions reported on Table IX were prepared.

TABLE IX

Compositions in dry powder. (The amounts of the components are expressed in per cent by weight).

| Components | Composition No. | | |
| --- | --- | --- | --- |
|  | 15 | 16 | 17 |
| Compound A | 3 | 0.5 | 0.1 |
| Mancozeb | | 5 | 10 |
| Synthetic silica | 3 | 3.5 | 3.9 |
| Talc | 94 | 91 | 86 |

EXAMPLE 7

Determination of fungicidal activity of compositions.

General procedure:

In a vineyard in natural conditions subjected to natural infection by *Plasmopara viticola*, the vine plants (cv. Lambrusco Ancellotta) have been randomly parceled in blocks having 4–5 plants each. Some of the parcels have been treated by spraying with aqueous suspensions of the wettable powders of Example 5. Some other untreated parcels have been used as a check. The results reported on the following Table X have been evaluated 11 days after the treatment in the fruit-setting stage. The results have been expressed by the infection index consisting in the percentage reduction of infection corrected by considering the degree of infection by *Plasmopara v.* in the check series. It is worth noting that no phytotoxicity phenomena have been observed in the treated vine plants.

TABLE X

Fungicidal activity of compositions according to the invention against *Plasmopara v.* on vines.

| Composition No. (see Table VIII)[1] | Applied dose[2] (Kg/ha) | Percentage reduction of fungine infection on | |
| --- | --- | --- | --- |
|  |  | leaves | grapes |
| 11 | 1.56 | 94.0% | 95.6% |
| 12 | 1.5 | 96.3% | 99.8% |
| 13 | 1.56 | 96.3% | 99.9% |
| 14 | 1.5 | 99.5% | 99.8% |

Notes to Table X:
[1]Similar results have been obtained by using all the compositions of Table VIII.
[2]Dose of composition.

What is claimed is:

1. A synergistic mixture of fungicides consisting of (A) N-(2,6-dimethylphenyl)-N-(1-methoxycarbonylethyl)-phenyl-acetamide and of (B) a dithiocarbamate selected from the group consisting of zinc-ethylene-bis-dithiocarbamate (Zineb) and manganese and zinc-ethylene-bis-dithiocarbamate (Mancozeb) in a ratio of (A) to (B) ranging from 1:3 to 1:200.

2. A fungicidal composition containing, as active ingredient, an effective amount of a synergistic mixture according to claim 1 and an inert carrier.

3. A fungicidal composition according to claim 2, in whch the synergistic mixture of active substances is contained in amounts ranging from 10 to 90% by weight.

4. A method of controlling fungi infections of useful plants, consisting in distributing on the plants a fungicidal composition according to claims 2 or 3 in amounts of from 1 to 30 Kg/ha.

5. The method of claim 4 in which the infection is due to *Plasmopara viticola* on vine plants.

* * * * *